(12) United States Patent
Bhowmick et al.

(10) Patent No.: US 12,016,585 B2
(45) Date of Patent: Jun. 25, 2024

(54) MEDICAL DEVICE HANDLE ASSEMBLIES AND METHODS OF USING THE SAME

(71) Applicant: Boston Scientific Medical Device Limited, Galway (IE)

(72) Inventors: Nabarun Bhowmick, Kolkata (IN); Deepak Kumar Sharma, Muzaffarnafar (IN); Shrikant Vasant Raut, Mumbai (IN); Subodh Morey, Ponda (IN); Charudatta Chandrakant Aradhye, Gurgaon (IN)

(73) Assignee: Boston Scientific Medical Device Limited, Galway (IE)

( * ) Notice: Subject to any disclaimer, the term of this patent is extended or adjusted under 35 U.S.C. 154(b) by 33 days.

(21) Appl. No.: 17/196,815

(22) Filed: Mar. 9, 2021

(65) Prior Publication Data
US 2021/0282797 A1    Sep. 16, 2021

Related U.S. Application Data

(60) Provisional application No. 62/987,694, filed on Mar. 10, 2020.

(51) Int. Cl.
*A61B 17/29*    (2006.01)
*A61B 17/00*    (2006.01)

(52) U.S. Cl.
CPC .............. *A61B 17/2909* (2013.01); *A61B 2017/00314* (2013.01); *A61B 2017/00323* (2013.01);
(Continued)

(58) Field of Classification Search
CPC ...... A61B 17/2909; A61B 2017/00314; A61B 2017/00323; A61B 2017/00367;
(Continued)

(56) References Cited

U.S. PATENT DOCUMENTS 5,674,230 A * 10/1997 Tovey ................ A61B 17/0469
606/139
9,277,932 B2 * 3/2016 Slater ................ A61B 17/3201
(Continued)

FOREIGN PATENT DOCUMENTS

EP        2027811 A1    2/2009
KR   101831068 B1 * 11/2016    ......... A61B 1/00147

OTHER PUBLICATIONS

International Search Report and Written Opinion in International Application No. PCT/IB2021/051967, dated Jun. 4, 2021 (10 pages).

*Primary Examiner* — Shaun L David
*Assistant Examiner* — Rachael L Geiger
(74) *Attorney, Agent, or Firm* — Bookoff McAndrews PLLC

(57) ABSTRACT

A medical device may include a handle including a fixed body and a movable body. The movable body may be movable relative to the fixed body. The medical device may include a shaft extending from the fixed body and an end effector at a distal end of the shaft. Rotation of the movable body relative to the fixed body may permit rotation of the end effector relative to the shaft, and rotation of the movable body with rotation of the fixed body may permit rotation of the end effector with the shaft. Deflection of the movable body relative to the fixed body may permit deflection of the end effector relative to the fixed body.

20 Claims, 6 Drawing Sheets

(52) U.S. Cl.
CPC ............... *A61B 2017/00367* (2013.01); *A61B 2017/00438* (2013.01)

(58) Field of Classification Search
CPC .... A61B 2017/00438; A61B 2017/291; A61B 2017/2927; A61B 2017/2929; A61B 1/0014
See application file for complete search history.

(56) References Cited

U.S. PATENT DOCUMENTS

| | | | |
|---|---|---|---|
| 2007/0021737 A1* | 1/2007 | Lee .................. | A61B 17/22 606/1 |
| 2007/0282371 A1* | 12/2007 | Lee .................. | A61B 17/29 606/205 |
| 2009/0054734 A1* | 2/2009 | DeSantis ............ | A61B 17/2909 600/153 |
| 2017/0007224 A1 | 1/2017 | Sholev et al. | |

\* cited by examiner

MEDICAL DEVICE HANDLE ASSEMBLIES AND METHODS OF USING THE SAME

CROSS-REFERENCE TO RELATED APPLICATIONS

This application claims the benefit of priority from U.S. Provisional Application No. 62/987,694, filed on Mar. 10, 2020, which is incorporated by reference herein in its entirety.

TECHNICAL FIELD

Various aspects of the disclosure relate generally to medical systems, devices, and related methods. More specifically, at least certain examples of the disclosure relate to systems, devices, and related methods for positioning and/or controlling one or more medical devices within a subject during a procedure via a handle assembly, among other aspects.

BACKGROUND

Technological developments have given users of medical systems, devices, and methods, the ability to conduct increasingly complex procedures on subjects. One challenge in the field of minimally invasive surgeries such as endoscopy, laparoscopy, and thoracoscopy, among other surgical procedures, is associated with providing control of medical devices during a procedure. Placement of such medical devices within a subject may be difficult. Additionally, actuating various medical systems that control a placement of such medical devices may be counterintuitive or complex to understand. The limitations on medical devices that facilitate access of other devices into a subject for placement may prolong the procedure, limit its effectiveness, and/or cause injury to the subject due to device failure or breakage. There is a need for devices and methods that address one or more of these difficulties or other related problems.

SUMMARY

Aspects of the disclosure relate to, among other things, systems, devices, and methods for accessing a target treatment site with a medical apparatus having intuitive handle assemblies that facilitate positioning of the apparatus, among other aspects. Each of the aspects disclosed herein may include one or more of the features described in connection with any of the other disclosed aspects.

According to an example, a medical device may include a handle including a fixed body and a movable body, wherein the movable body is movable relative to the fixed body. The medical device may include a shaft extending from the fixed body and an end effector at a distal end of the shaft. Rotation of the movable body relative to the fixed body may permit rotation of the end effector relative to the shaft, and rotation of the movable body with rotation of the fixed body may permit rotation of the end effector with the shaft. Deflection of the movable body relative to the fixed body may permits deflection of the end effector relative to the fixed body.

Any of the medical devices described herein may have any one or more of the following features. The handle may include one or more actuators for transitioning the handle from an unactuated state to an actuated state. The one or more actuators may be sized to receive at least one finger or digit of a user. The one or more actuators may include a coupler disposed within the handle and coupled to a slider that may be received within an inner slot of the handle. In the actuated state of the handle, the one or more couplers may be configured to move the slider to a proximal end of the inner slot. The medical device may further include a rotation joint disposed within and fixed to the handle, wherein the rotation joint may be coupled to a first end of an actuation wire, wherein a second end of the actuation wire may be coupled to the end effector. The rotation joint may be configured to rotate the actuation wire and the end effector in response to rotation of the movable body relative to the fixed body. The medical device may further include a lock configured to fix the movable body relative to the fixed body such that rotation of the movable body may provide rotation of the fixed body. The medical device may further include a pair of drive wires coupled to and extending between the movable body and the distal end of the shaft. The movable body may be configured to translate the pair of drive wires within the movable body to deflect the end effector relative to the fixed body when the movable body is deflected relative to the fixed body. The medical device may further include an actuation wire coupled to and extending between the movable body and the end effector. In an actuated state of the handle, the actuation wire may be tensioned so as to actuate the end effector. The end effector may include a pair of jaws, and wherein in the actuated state, the pair of jaws may be closed and/or approximate one another. The medical device may further include a connector assembly including a first clasp and a second clasp, wherein the first clasp is operable to attach the connector assembly to the handle and the second clasp is operable to attach the connector assembly to an instrument, thereby fixing the handle relative to the instrument.

According to another example, a medical device may include a shaft assembly, an end effector at a distal end of the shaft assembly, and a handle at a proximal end of the shaft assembly. The handle may include a proximal portion and a distal portion. The handle may be configured such that rotation of the proximal portion relative to the distal portion may rotate the end effector relative to the shaft assembly, and simultaneous rotation of the proximal portion and the distal portion may rotate the end effector and the shaft assembly together. The handle may be configured such that deflection of the proximal portion relative to the distal portion may deflect the end effector relative to the shaft assembly.

Any of the medical devices described herein may have any one or more of the following features. The handle may include an actuator extending laterally outward from the proximal portion. The handle may be configured such that translation of the actuator inward relative to the proximal portion may actuate the end effector to a first configuration, and translation of the actuator outward relative to the proximal portion may actuate the end effector to a second configuration. The medical device may further include an actuation wire including a first end coupled to the proximal portion and a second end coupled to the end effector. The actuation wire may be configured to rotate the end effector in response to rotation of the proximal portion relative to the distal portion. The medical device may further include a pair of drive wires, each of the drive wires may include a first end coupled to the proximal portion and a second end coupled to the end effector. The pair of drive wires may be configured to deflect the end effector relative to the shaft assembly in response to deflection of the proximal portion relative to the distal portion. The medical device may further include a lock configured to rotatably fix the proximal portion relative to the distal portion, such that rotation of the proximal portion may provide simultaneous rotation of the distal portion.

According to another example, a medical device may include a first body and a second body extending distally from the first body. The first body may be laterally pivotable and rotatable relative to the second body. The medical device may include an end effector extending distally from the second body. The first body may be configured to rotate the end effector relative to the second body when the first body rotates independent of the second body, and rotate the end effector with the second body when the first body rotates concurrently with the second body. The first body may be configured to pivot the end effector relative to the second body when the first body pivots independent of the second body.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of the disclosure and together with the description, serve to explain the principles of the disclosure.

DETAILED DESCRIPTION

Figure 1:
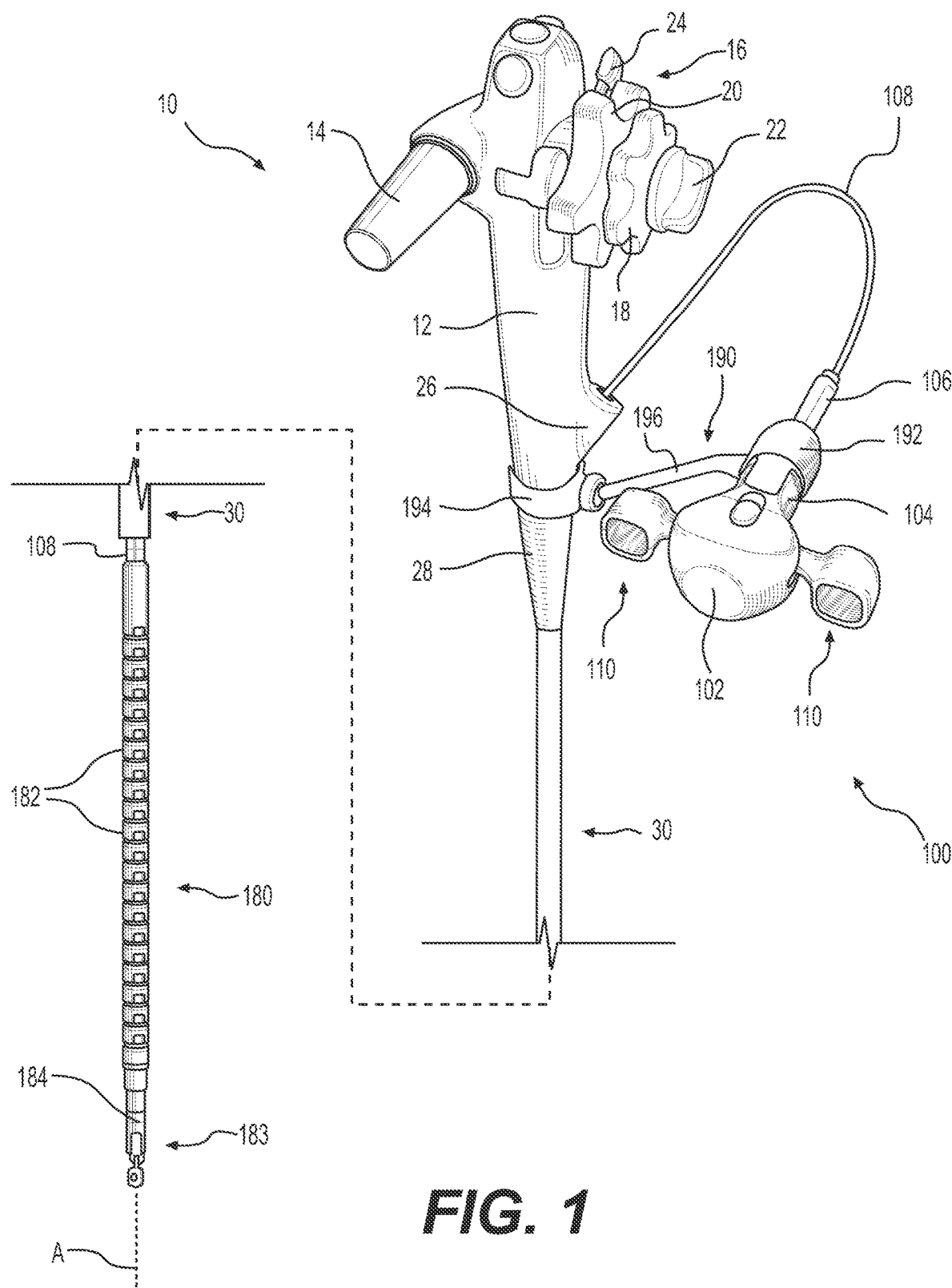
FIG. 1 is a perspective view of an exemplary medical device and a medical instrument, with the medical device having a handle assembly and a grasper assembly, according to aspects of this disclosure.

Examples of the disclosure include systems, devices, and methods for controlling multiple components of a medical instrument at a target site within the body, where the components generally require manipulation to access a target site, among other aspects. Reference will now be made in detail to aspects of the disclosure, examples of which are illustrated in the accompanying drawings. Wherever possible, the same or similar reference numbers will be used through the drawings to refer to the same or like parts. The term "distal" refers to a portion farthest away from a user when introducing a device into a subject (e.g., a patient). By contrast, the term "proximal" refers to a portion closest to the user when placing the device into the subject. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." As used herein, the terms "about," "substantially," and "approximately," indicate a range of values within +/−10% of a stated value.

Examples of the disclosure may be used to facilitate a control and positioning of tools/devices (end effector) of a medical instrument at a target treatment site by providing one or more mechanisms and/or assemblies for positioning said tools/devices at the target treatment site. For instance, some examples combine a handle assembly on a medical device for selective control and/or manipulation of components of the medical device, such as, for example, an end effector (e.g., grasper assembly). The medical device may further include a movable body coupled to a fixed body, with the movable body further coupled to the handle assembly opposite of the fixed body. The handle assembly may be configured such that rotation of the handle assembly relative to the movable body provides a rotation of the grasper assembly relative to the movable body and the fixed body. The handle assembly may be further configured such that pivoting the handle assembly relative to the fixed body provides an articulation of the grasper assembly relative to the fixed body. Further, the handle assembly may be configured such that manipulating one or more actuators of the handle assembly relative to the movable body may provide an actuation of the end effector.

Examples of the disclosure may relate to devices and methods for performing various medical procedures and/or treating portions of the large intestine (colon), small intestine, cecum, esophagus, any other portion of the gastrointestinal tract, and/or any other suitable subject (e.g., patient) anatomy (collectively referred to herein as a "target treatment site"). The device and related methods may be used laparoscopically or endoscopically, or in any other open or minimally invasive procedure, including thorascopic and ENT procedures. Reference will now be made in detail to examples of the present disclosure described above and illustrated in the accompanying drawings. Wherever possible, the same reference numbers will be used throughout the drawings to refer to the same or like parts.

FIG. 1 shows a schematic depiction of an exemplary medical device 100 in accordance with an example of this disclosure. The medical device 100 may include a handle assembly 102, a movable body 104, and a fixed body 106. In the example, the movable body 104 extends distally from, and/or is coupled to, a distal end of the handle assembly 102. Further, the fixed body 106 extends distally from, and/or is coupled to, a distal end of the movable body 104. Accordingly, it should be understood that the movable body 104 of the medical device 100 is disposed between the handle assembly 102 and the fixed body 106. As described in greater detail herein, the handle assembly 102 is at least partially movable relative to the movable body 104 and/or the fixed body 106, and the movable body 104 is at least partially movable relative to the fixed body 106. In other examples, the handle assembly 102 and the movable body 104 may be a unitary component of the medical device 100 (e.g., a single feature) such that the handle assembly 102 is a proximal portion of the component and the movable body 104 is a distal portion of the component.

The medical device 100 may further include a shaft 108 extending distally from a distal end of the fixed body 106 such that the fixed body 106 is disposed between the shaft 108 and the movable body 104. The shaft 108 of the medical device 100 is flexibly deformable such that a size, a shape, and/or a configuration of the shaft 108 may be adjustable. The shaft 108 defines a longitudinal axis extending between a proximal end of the shaft 108, located adjacent to the fixed body 106, and a distal end of the shaft 108 located adjacent to an articulation joint 180 of the medical device 100. In the example, a proximal end of the shaft 108 is secured to, and/or coupled with, the fixed body 106 and a distal end of the shaft 108 is secured to, and/or coupled with, the articulation joint 180. Accordingly, and as described in further detail herein, the shaft 108 of the medical device 100 is configured to move (e.g., rotate) simultaneously with the fixed body 106 and the articulation joint 180.

Further, the medical device 100 may include one or more actuators 110 extending outwardly from (e.g., radially outwardly relative to a longitudinal axis of the handle assembly 102) and/or coupled to the handle assembly 102. In the example, a pair of actuators 110 may be disposed along opposing sidewalls of the handle assembly 102. It should be appreciated that additional and/or fewer actuators 110 may be included on various other walls and/or surfaces of the handle assembly 102 other than those shown and described herein without departing from a scope of this disclosure. The pair of actuators 110 are configured to actuate one or more components of the medical device 100, such as, for example, an end effector 183, as shown and described in further detail below.

Still referring to FIG. 1, the articulation joint 180 of the medical device 100 may include a plurality of articulation links 182 and a clevis 184. The plurality of articulation links 182 may be sequentially aligned with one another and at least partially define a longitudinal length of the articulation joint 180. In the example, the plurality of articulation links 182 are movably coupled to one another such that each of the plurality of articulation links 182 is configured to move (e.g., bend, pivot, deflect) relative to one another. In an unactuated state, a longitudinal length of the articulation joint 180 defined by the plurality of articulation links 182 may be substantially parallel to a longitudinal axis A of the articulation joint 180 (e.g., when the articulation joint is positioned in a neutral, undeflected configuration). As described above, a distal end of the shaft 108 may be positioned adjacent to and/or secured at a proximal end of the articulation joint 180, such as, for example, a first (e.g., proximal-most) articulation link 182 of the plurality of articulation links 182.

The clevis 184 may extend distally from and/or be coupled to a distal end of the articulation joint 180, such as, for example, a last (e.g., distal-most) articulation link 182 of the plurality of articulation links 182. In the example, the clevis 184 is rotatably coupled to the distal-most articulation link of the plurality of articulation links 182 such that the clevis 184 is at least partially rotatable relative to articulation joint 180. The end effector 183 of the medical device 100 extends distally from a distal end of the clevis 184 such that the end effector 183 is rotatable with the clevis 184 and relative to the articulation joint 180. It should be appreciated that the end effector 183 of the medical device 100 may include various suitable components, including, but not limited to, one or more clamps, forceps, clips, needles, shears, suturing devices, lighting devices, imaging systems, grasper assemblies, and various other suitable tools and/or devices. Accordingly, the end effector 183 shown and described herein is merely provided for exemplary purposes and may include various other configurations without departing from a scope of this disclosure. With the end effector 183 and the clevis 184 of the medical device 100 positioned relatively distal of the articulation joint 180, it should be understood that movement of the plurality of articulation links 182 may provide likewise movement (e.g., deflection) of the end effector 183 and the clevis 184 relative to at least a distal end of the shaft 108.

Still referring to FIG. 1, the medical device 100 may be used with one or more ancillary devices, such as, for example, a medical instrument 10. In the example shown and described herein, the medical instrument 10 may include an endoscope (e.g., duodenoscope), however, it should be appreciated that the medical device 100 may be utilized with various other ancillary devices. The medical instrument 10 may include, among other things, a handle 12, an umbilicus connection/port 14, one or more control knobs 16, a device port 26, a strain relief 28, and a shaft 30. The handle 12 of the medical instrument 10 may be sized, shaped, and configured to be manually grasped and/or maneuverable by a user of the medical instrument 10. The one or more control knobs 16 may include, for example, one or more articulation knobs 18, 20, an articulation lock 22, and an elevator actuator 24. The one or more articulation knobs 18, 20 may be configured and operable to articulate (e.g., move, bend, deflect, pivot) a distal end of the shaft 30 of the medical instrument 10 (e.g., adjacent to the articulation joint 180) relative to the strain relief 28.

By way of illustrative example, the medical instrument 10 may include a first articulation knob 18 for articulating a distal end of the shaft 30 in various radial directions (e.g., left and right) relative to the strain relief 28 and/or a proximal end of the shaft 30. The medical instrument 10 may further include a second articulation knob 20 for articulating a distal end of the shaft 30 in various longitudinal directions (e.g., up and down) relative to the strain relief 28 and/or a proximal end of the shaft 30. The articulation lock 22 of the medical instrument 10 may be configured and operable to lock the one or more articulation knobs 18, 20 to inhibit articulation of the shaft 30 relative to the strain relief 28. The elevator actuator 24 of the medical instrument 10 may be configured and operable to actuate one or more other components of the medical instrument 10, such as, for example, an elevator (not shown) at a distal portion of the shaft 30. It should be understood that the elevator may include an adjustable protrusion, lever, and/or ramp located adjacent to an opening at a distal portion of the shaft 30. The elevator may be configured to guide or direct a device outwardly from a distal portion of the shaft 30, such as, for example, a distal end of the shaft 108 of the medical device 100, the articulation joint 180, and/or the end effector 183. The strain relief 28 of the medical instrument 10 may be configured and operable to minimize, inhibit, and/or relieve pinch tension or kinking stresses of one or more devices received therethrough, such as, for example, the shaft 108 of the medical device 100.

Still referring to FIG. 1, in some examples, the medical device 100 may further include a connector assembly 190 that is configured and operable to secure the handle assembly 102, the movable body 104, and the fixed body 106 to the medical instrument 10. By way of example, the connector assembly 190 may include a first clasp 192, a second clasp 194, and an intermediate strap, bracket, and/or arm 196 disposed between the first clasp 192 and the second clasp 194. The second clasp 194 of the connector assembly 190 may include a ring, bracket, loop, or structure that is sized and shaped to receive the medical instrument 10, such as the handle 12 and/or the strain relief 28, for securing the connector assembly 190 thereto. The first clasp 192 of the connector assembly 190 may include a ring, bracket, loop, or structure that is sized and shaped to receive the medical device 100, such as the movable body 104 and/or the fixed body 106, for securing the connector assembly 190 thereto.

In other examples, the first clasp 192 and/or the second clasp 194 may be configured and operable to adjust a size and shape of the respective ring, bracket, loop, or structure in accordance with a size, shape, and/or configuration of an object/device to be grasped by the clasp 192, 194 (e.g., the handle 12, the strain relief 28, the movable body 104, and/or the fixed body 106). In this instance, at least the first clasp 192 and/or the second clasp 194 of the connector assembly 190 may be formed of a flexibly elastic material that is configured to be deformable. The intermediate arm 196 may be arranged to connect the first clasp 192 to the second clasp 194 and to maintain the clasps 192, 194 in a relative position to one another. It should be appreciated that the intermediate arm 196 may be formed of a rigid material relative to the first clasp 192 and/or the second clasp 194 such that the intermediate arm 196 may be configured to suspend an object/device received in the second clasp 194 (e.g., the medical device 100) relative to an object/device received in the first clasp 192 (e.g., the medical instrument 10), and vice versa. In some examples, the connector assembly 190 is configured and operable to adjust a size, shape, and/or configuration of the intermediate arm 196 to thereby modify a respective position of the clasps 192, 194 relative to one another.

Figure 2A:
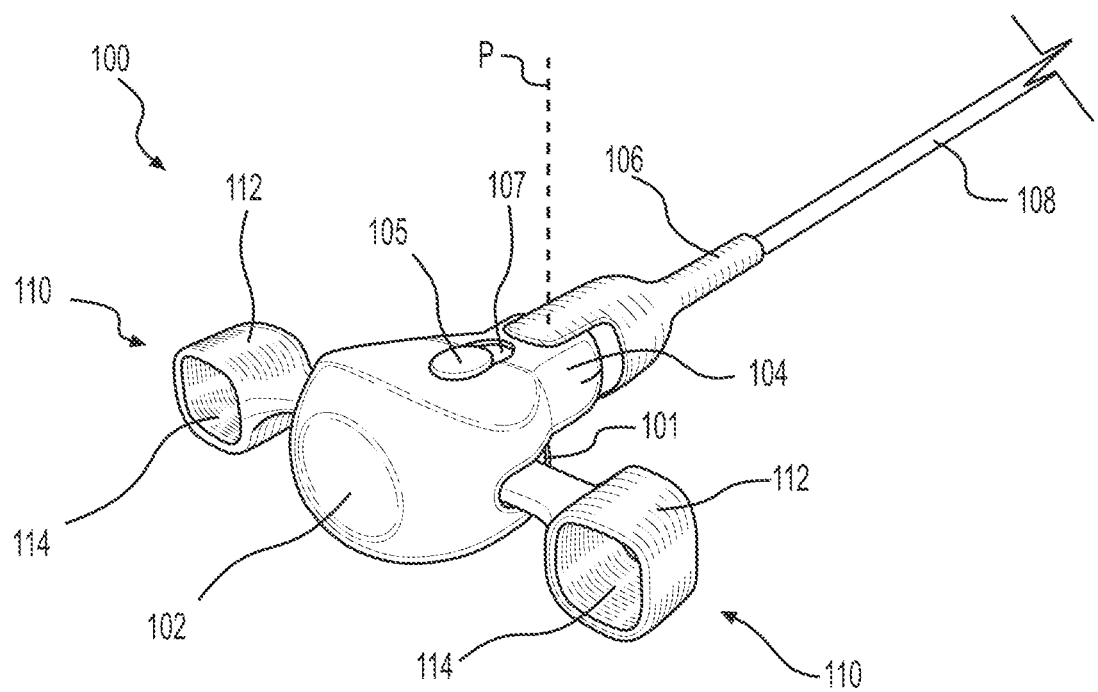
FIG. 2A is a partial perspective view of the medical device of FIG. 1, with the medical device in a neutral position, according to aspects of this disclosure.
Figure 2B:
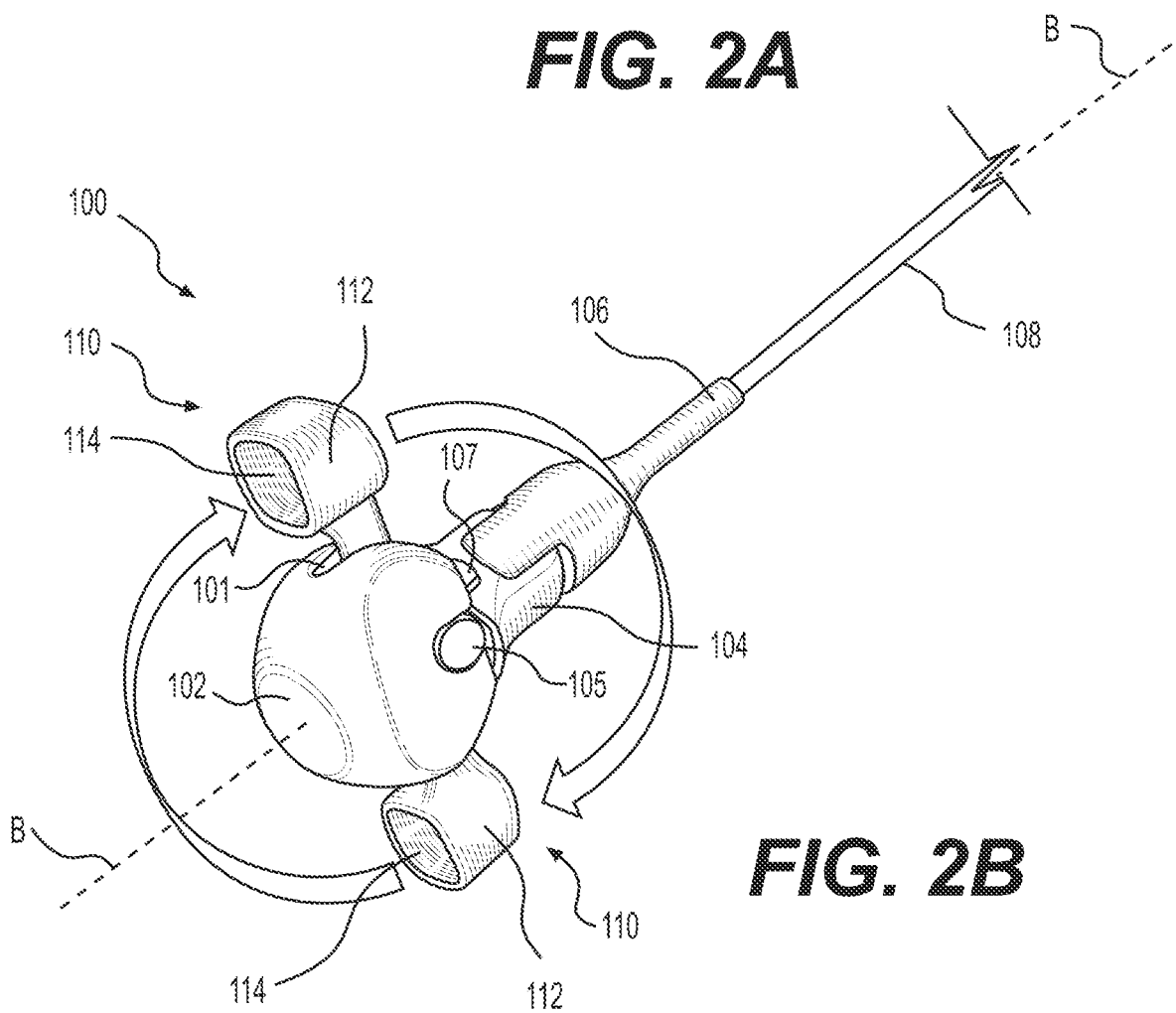
FIG. 2B is a partial perspective view of the medical device of FIG. 1, with the medical device in a rotated position, according to aspects of this disclosure.

Referring now to FIGS. 2A-2B, and as described above, the movable body 104 is movable relative to the fixed body 106. For instance, the movable body 104 may be secured to and/or coupled with the fixed body 106 about a pivot joint that defines a pivot axis P. In the example, the pivot axis P of the pivot joint is relatively transverse (e.g., substantially perpendicular) to a central axis B of the fixed body 106 (FIG. 2B). As described in greater detail herein, the movable body 104 is configured to move (e.g., pivot) relative to the fixed body 106 about the pivot axis P of the pivot joint (FIGS. 5A-6B). The movable body 104 is pivotable along a lateral plane that is parallel to the central axis B of the fixed body 106 and transverse to the pivot axis P of the pivot joint.

The medical device 100 further includes a lock assembly 105 disposed within a slot 107 that is positioned along the handle assembly 102 and the movable body 104. In the example, at least a portion of the slot 107 is formed along a top surface of the handle assembly 102 and a top surface of the movable body 104. The lock assembly 105 is configured to move relative to the slot 107 to lock and/or unlock the handle assembly 102 and the movable body 104 to one another. In other words, the lock assembly 105 of the medical device 100 is operable to transition the handle assembly 102 and the movable body 104 between a locked state and an unlocked state. In the locked state, relative movement between the handle assembly 102 and the movable body 104 may be inhibited. Additionally, in the unlocked state, relative movement between the handle assembly 102 and the movable body 104 may be permitted.

For example, the medical device 100 is in a locked state when the lock assembly 105 is translated distally relative to the slot 107 and positioned at least partially on a portion of the slot 107 along the handle assembly 102 and the movable body 104 (e.g., such that the lock assembly 105 spans a transition between the handle assembly 102 and the movable body 104). In this instance, the medical device 100 is configured such that rotation of the handle assembly 102 may provide a simultaneous rotation of the movable body 104 and the fixed body 106. With the shaft 108 extending from the fixed body 106 and the articulation joint 180 extending from the shaft 108, rotation of the fixed body 106 may provide a likewise rotation of the articulation joint 180 and/or the end effector 183. Accordingly, the handle assembly 102 is configured and operable to rotate at least the articulation joint 180 and/or the end effector 183 when the medical device 100 is in the locked state.

As shown in FIG. 2A, the medical device 100 is in an unlocked state when the lock assembly 105 is translated proximally relative to the slot 107 and onto the portion of the slot 107 along the handle assembly 102. In this instance, the lock assembly 105 is removed from the portion of the slot 107 disposed along the movable body 104 (e.g., no portion of lock assembly 105 spans any portion of movable body 104). With the medical device 100 in the unlocked state, the handle assembly 102 is operable to move (e.g., rotate) relative to and independently of the movable body 104, as seen in FIG. 2B. In this instance, the handle assembly 102 is configured to rotate about the central axis B of the fixed body 106 and relative to the movable body 104, the fixed body 106, and/or the shaft 108. In other words, the movable body 104, the fixed body 106, and the shaft 108 may remain fixed as the handle assembly 102 rotates (e.g., clockwise, counter-clockwise, etc.) about the central axis B of the fixed body 106. As described further herein, the medical device 100 may be configured such that rotation of the handle assembly 102 relative to the movable body 104 and the fixed body 106 may provide rotation of the end effector 183 relative to the shaft 108 and the articulation joint 180.

Figure 3A:
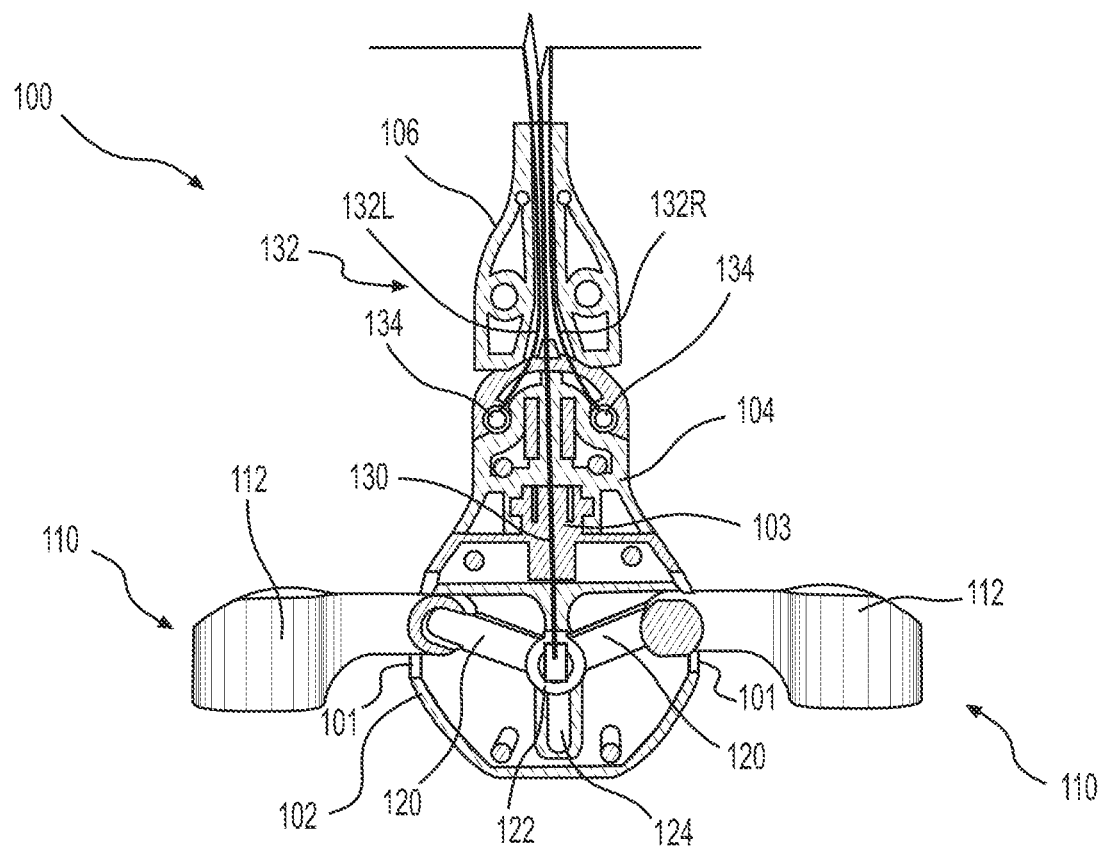
FIG. 3A is a cross-sectional top view of the medical device of FIG. 1 in an unactuated state, according to aspects of this disclosure.

Referring now to FIG. 3A, the medical device 100 includes a rotation joint 103 disposed at least partially within, and extending between, the handle assembly 102 and the movable body 104. The rotation joint 103 is operable to rotatably couple the handle assembly 102 to the movable body 104 and defines the central axis B of the fixed body 106. In the example, the rotation joint 103 is fixed relative to the handle assembly 102 and is rotatable relative to the movable body 104, such that the rotation joint 103 rotates relative to, and within, the movable body 104 with the handle assembly 102. It should be appreciated that in other examples the rotation joint 103 may be configured in an opposite configuration, such that the rotation joint 103 is fixed relative to the movable body 104 and is rotatable relative to the handle assembly 102. In that instance, the rotation joint 103 rotates relative to, and within, the handle assembly 102 with the movable body 104 when the medical device 100 is in the unlocked state.

Referring back to FIGS. 2A-2B, the handle assembly 102 is operable to rotate in response to a user actuating the pair of actuators 110 of the medical device 100. As described above, each of the actuators 110 extend outwardly from the handle assembly 102 along opposing sidewalls of the handle assembly 102. The handle assembly 102 includes at least one opening 101 disposed along each sidewall of the handle assembly 102 for receiving the actuator 110 therethrough. In this instance, at least a portion of the actuator 110 extends into the handle assembly 102. It should be understood that the openings 101 are sized and shaped to be larger than a portion of the actuators 110 extending therethrough such that each of the actuators 110 is operable to move relative to the opening 101 of the handle assembly 102. For example, the actuators 110 may be translated through the openings 101 to actuate one or more components of the medical device 100, such as, for example, the end effector 183. As described in further detail herein, the portion of the actuator 110 received within the handle assembly 102 is operable to interact with one or more internal components disposed in the handle assembly 102 (FIGS. 3A-4B).

With respect to a portion of the actuators 110 disposed externally of the handle assembly 102, each of the actuators 110 includes an exterior housing 112 defining a channel 114. The exterior housing 112 is sized and shaped in accordance with a digit and/or finger of a user of the medical device 100 such that each of the actuators 110 is configured to receive a digit and/or finger (e.g., index/forefinger, middle finger, thumb, etc.) within the channel 114. In some examples, the exterior housing 112 may be formed of a flexibly elastic material such that the exterior housing 112 is configured to deform in accordance to a size, shape, and/or profile of a digit and/or finger received within the channel 114 of the actuator 110. In other examples, the exterior housing 112 and/or the channel 114 of the actuators 110 may include various other suitable sizes, shapes, and/or configurations than those shown and described herein. A location of the actuators 110 relative to the handle assembly 102 may be configured to maintain a user's hand and/or forearm in an ergonomic position during use of the handle assembly 102, such as, for example, in a neutral wrist position when actuating the end effector 183.

Referring again to FIG. 3A, the medical device 100 is depicted with a top surface/wall of the handle assembly 102, the movable body 104, and the fixed body 106 omitted to show the one or more internal components disposed therein. As described above, at least a portion of the actuators 110 extend into the handle assembly 102 and interact with one or more internal components of the handle assembly 102. For instance, each of the actuators 110 includes a coupler 120 disposed within the handle assembly 102. In some examples, the handle assembly 102 includes one or more grooves disposed within a cavity of the handle assembly 102 that are sized and shaped to receive each of the pair of couplers 120 therein. The one or more grooves may be configured to guide and/or constrain a relative movement of the couplers 120 within the handle assembly 102.

In the example, the coupler 120 is coupled to the actuator 110 at a first end of the coupler 120, and further coupled to a slider 122 at an opposite end of the coupler 120. Accordingly, the pair of couplers 120 form a kinematic coupling between the actuators 110 and the slider 122. The slider 122 is received within a slot 124 and is configured to move (e.g., translate) relative to the slot 124. It should be understood that with the couplers 120 secured to the actuators 110, and the actuators 110 being configured to move as described above, the couplers 120 are operable to move the slider 122 within and/or along the slot 124 in response to movement of the actuators 110.

The handle assembly 102 further includes one or more actuation wires 130 and drive wires 132 disposed therein. In the example, the handle assembly 102 includes an actuation wire 130 secured and/or coupled to the slider 122 at a first, proximal end of the actuation wire 130. The actuation wire 130 has a longitudinal length and extends through the handle assembly 102, the movable body 104, and the fixed body 106. Further, the actuation wire 130 extends through the rotation joint 103, and is fixed relative to the rotation joint 103. With the rotation joint 103 fixed relative to the handle assembly 102, as described above, it should be understood that rotation of the rotation joint 103 and the handle assembly 102 may provide a simultaneous rotation of the actuation wire 130.

Although not shown, it should be understood that the actuation wire 130 may extend through the shaft 108 of the medical device 100 (FIGS. 1-2B), through the articulation joint 180, and a second, distal end of the actuation wire 130 may be secured and/or coupled to the end effector 183 of the medical device 100. As described further herein, the actuation wire 130 may be configured to actuate the end effector 183 of the medical device 100 in response to an actuation the pair of actuators 110. Additionally, the actuation wire 130 may be further configured to rotate the end effector 183 relative to the shaft 108 and/or the articulation joint 180 in response to rotation of the handle assembly 102 relative to the movable body 104 and/or the fixed body 106.

Still referring to FIG. 3A, the medical device 100 includes a pair of drive wires 132 (e.g., a left drive wire 132L and a right drive wire 132R) secured and/or coupled to the movable body 104 at respective connection points 134. Each of the drive wires 132 have a longitudinal length that extends at least partially through the movable body 104 and the fixed body 106. Although not shown, it should be understood that the drive wires 132 may extend through the shaft 108 of the medical device 100 (FIGS. 1-2B) and a second, distal end of each of the drive wires 132 may be secured and/or coupled to the articulation joint 180 of the medical device 100. For instance, a distal end of the drive wires 132 may be secured to a distal-most articulation link 182 of the plurality of articulation links 182, such as, for example, on opposing sides/portions of the distal-most articulation link 182. As described further herein, the pair of drive wires 132 may be configured to articulate the articulation joint 180 of the medical device 100, such as the plurality of articulation links 182, in response to actuation of the handle assembly 102.

Figure 3B:
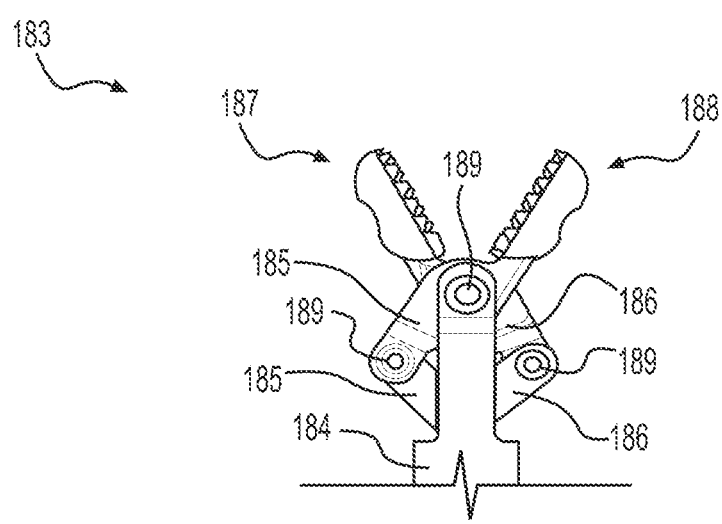
FIG. 3B is a partial top view of the grasper assembly of the medical device of FIG. 1 in an unactuated state, according to aspects of this disclosure.

Referring now to FIG. 3B, the end effector 183 of the medical device 100 may include a plurality of first links 185, a plurality of second links 186, a first jaw 187, and a second jaw 188. At least one of the plurality of first links 185 (e.g., a proximal-most first link 185) is movably coupled to the clevis 184 and at least one of the plurality of second links 186 (e.g., a proximal-most second link 186) is movably coupled to the clevis 184. In the example, at least one of the plurality of first links 185 (e.g., a distal-most first link 185) may be movably coupled to a proximal end of the second jaw 188 and at least one of the plurality of second links 186 (e.g., a distal-most second link 186) may be movably coupled to a proximal end of the first jaw 187. In other examples, the first links 185 and the second links 186 may be arranged such that at least one of the plurality of first links 185 (e.g., a distal-most first link 185) is movably coupled to a proximal end of the first jaw 187, and at least one of the plurality of second links 186 (e.g., a distal-most second link 186) is movably coupled to a proximal end of the second jaw 188. As described above, it should be understood that the pair of jaws 187, 188 may be interchangeable with various other suitable end effectors and operable via the clevis 184 or other movable element.

Each of the plurality of first links 185 and each of the plurality of second links 186 may include a pivot joint 189 at opposing, terminal ends of the links 185, 186, respectively. Accordingly, each of the plurality of first links 185 may be movably (e.g., rotatably) coupled to one another at opposing ends of the first links 185 via respective pivot joints 189. Each of the plurality of second links 186 may be movably (e.g., rotatably) coupled to one another at opposing ends of the second links 186 via respective pivot joints 189. Further, the distal-most first link 185 is movably coupled to the second jaw 188 via the pivot point 189, and the distal-most second link 186 is movably coupled to the first jaw 187 via the pivot point 189.

Still referring to FIG. 3B, in the example, the end effector 183 includes a pair of first links 185 and a pair of second links 186. Accordingly, the proximal-most first link 185 is movably coupled to the distal-most first link 185 by engaging the respective pivot joints 189 of each first link 185 to one another. The proximal-most second link 186 is movably coupled to the distal-most second link 186 by engaging the respective pivot joints 189 of each second link 186 to one another. It should be understood that the end effector 183 may include additional and/or fewer links 185, 186 than those shown and described herein without departing from a scope of this disclosure. The proximal-most first link 185 and the proximal-most second link 186 may be secured to and/or coupled with a distal end of the actuation wire 130 at the respective pivot joints 189 (e.g., a proximal-most pivot joint 189) of each link 185, 186.

It should be appreciated that the actuation wire 130 may be coupled to the proximal-most links 185, 186 within and/or through the clevis 184. As described in greater detail below, movement of the actuation wire 130 (e.g., axial translation) relative to the handle assembly 102, the movable body 104, the fixed body 106, and/or the shaft 108 may provide movement of the plurality of links 185, 186 (including the proximal-most links 185, 186, the distal-most links 185, 186, and the like). With the plurality of links 185, 186 coupled to the jaws 187, 188 of the end effector 183, movement of the actuation wire 130 may further provide movement of the pair of jaws 187, 188 relative to the clevis 184 and/or to one another.

According to an exemplary method of using the medical device 100, the medical instrument 10 may be used to facilitate access to a target treatment site within a subject by positioning the shaft 30 adjacently thereto. The medical device 100 may be used for various suitable procedures, including, but not limited to, endoluminal surgical procedures such as endoscopic mucosal resection (EMR), endoscopic submucosal dissection (ESD), pre-oral endoscopic myotomy (POEM), and the like. It should be understood that the steps of the exemplary method described herein, and the sequence in which they are presented, are merely illustrative such that additional and/or fewer steps may be included without departing from a scope of this disclosure. It should further be appreciated that the exemplary method of utilizing the medical device 100 described and shown herein may be employed for various other procedures and used with various other medical systems, devices, instruments, and/or assemblies than the medical instrument 10 described herein.

As shown in FIG. 1, the shaft 108 of the medical device 100 may be inserted into the medical instrument 10 and received in the shaft 30 via the device port 26. The shaft 108 of the medical device 100 may be advanced through the shaft 30 of the medical instrument 10 such that the articulation joint 180 and the end effector 183 may extend distally outward from a distal end of the shaft 30. The medical device 100 may be secured to the medical instrument 10 by the connector assembly 190 as shown and described above. With the end effector 183 positioned adjacent to the target treatment site (not shown), a user of the medical device 100 may actuate the handle assembly 102 during a procedure to treat the target site with the end effector 183.

Referring to FIG. 2A, the medical device 100 is depicted in an unactuated configuration with the handle assembly 102 aligned with the movable body 104 and the fixed body 106. During use of the medical device 100 a user may transition the medical device 100 between the locked state and the unlocked state by actuating the lock assembly 105. As described in detail above, rotation of the handle assembly 102 with the medical device 100 in the locked state provides a rotation of the movable body 104 and the fixed body 106. With the shaft 108 extending from the fixed body 106, and the articulation joint 180 extending from the shaft 108, the handle assembly 102 is configured to simultaneously rotate the shaft 108 and the articulation joint 180 with the movable body 104 and the fixed body 106 in the locked state. Further, with the end effector 183 coupled to a distal end of the actuation wire 130 and the actuation wire 130 fixed to the handle assembly 102 at the rotation joint 103, the handle assembly 102 may further rotate the end effector 183.

Referring to FIG. 2B, with the medical device 100 in the unlocked state, rotation of the handle assembly 102 may provide rotation of the actuation wire 130 relative to and independent of the movable body 104, the fixed body 106, the shaft 108, and/or the articulation joint 180. As described in detail above, the rotation joint 103 disposed within the handle assembly 102 facilitates independent rotation of the handle assembly 102 relative to the movable body 104. With the actuation wire 130 coupled to the end effector 183 and fixed at the rotation joint 103, the end effector 183 is operable to rotate along the central axis B of the fixed body 106 in response to rotating the handle assembly 102 (e.g., in a clockwise direction, counter-clockwise direction, and the like).

Referring to FIGS. 3A-3B, the medical device 100 is depicted in an unactuated state with the pair of actuators 110 in a fully extended state relative to the handle assembly 102. Further, the pair of jaws 187, 188 is depicted in an open configuration when the actuators 110 are in an unactuated state. In this instance, the slider 122 is positioned along a distal end of the slot 124 such that the actuation wire 130 is extended distally relative to the handle assembly 102, the movable body 104, the fixed body 106, and/or the shaft 108. The medical device 100 is further depicted in a linear configuration, with the handle assembly 102 positioned and/or oriented in a substantially parallel arrangement with the movable body 104 and the fixed body 106.

Figure 4A:
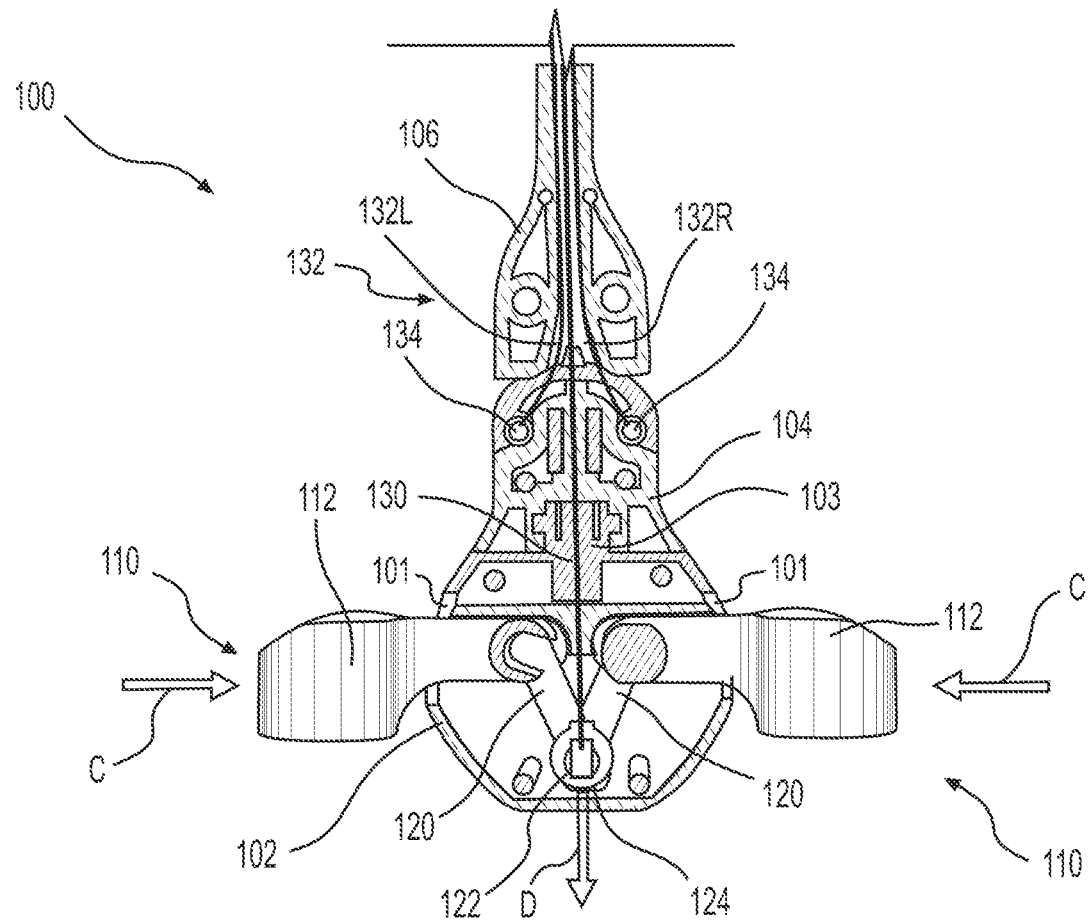
FIG. 4A is a cross-sectional top view of the medical device of FIG. 1 in an actuated state, according to aspects of this disclosure.
Figure 4B:
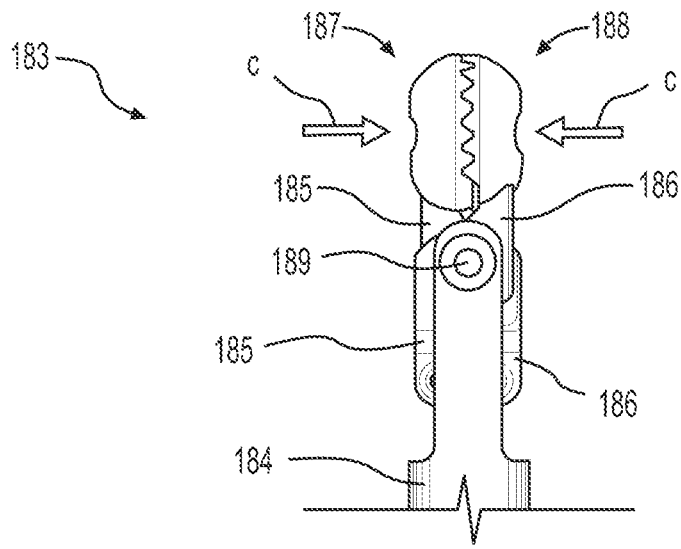
FIG. 4B is a partial top view of the grasper assembly of the medical device of FIG. 1 in an actuated state, according to aspects of this disclosure.

Referring now to FIGS. 4A-4B, the medical device 100 is depicted in an actuated state with the pair of actuators 110 in a compressed state relative to the handle assembly 102. Further, the pair of jaws 187, 188 is depicted in a closed configuration when the actuators 110 are in an actuated state. In other words, the pair of actuators 110 are translated (e.g., pushed) inwardly in a direction C through the openings 101 of the handle assembly 102. As a result, the slider 122 is translated proximally in a direction D and positioned along a proximal end of the slot 124. When the medical device 100 is in the actuated state, the actuation wire 130 is retracted proximally relative to the handle assembly 102, the movable body 104, the fixed body 106, and/or the shaft 108. In this instance, the actuation wire 130 moves proximally and pulls the plurality of first links 185 and the plurality of second links 186 in the direction D. In response, the plurality of links 185, 186 may move (e.g., pivot) about the respective pivot points 189 and relative to one another to move the pair of jaws 187, 188 in the direction C to the closed configuration.

Figure 5A:
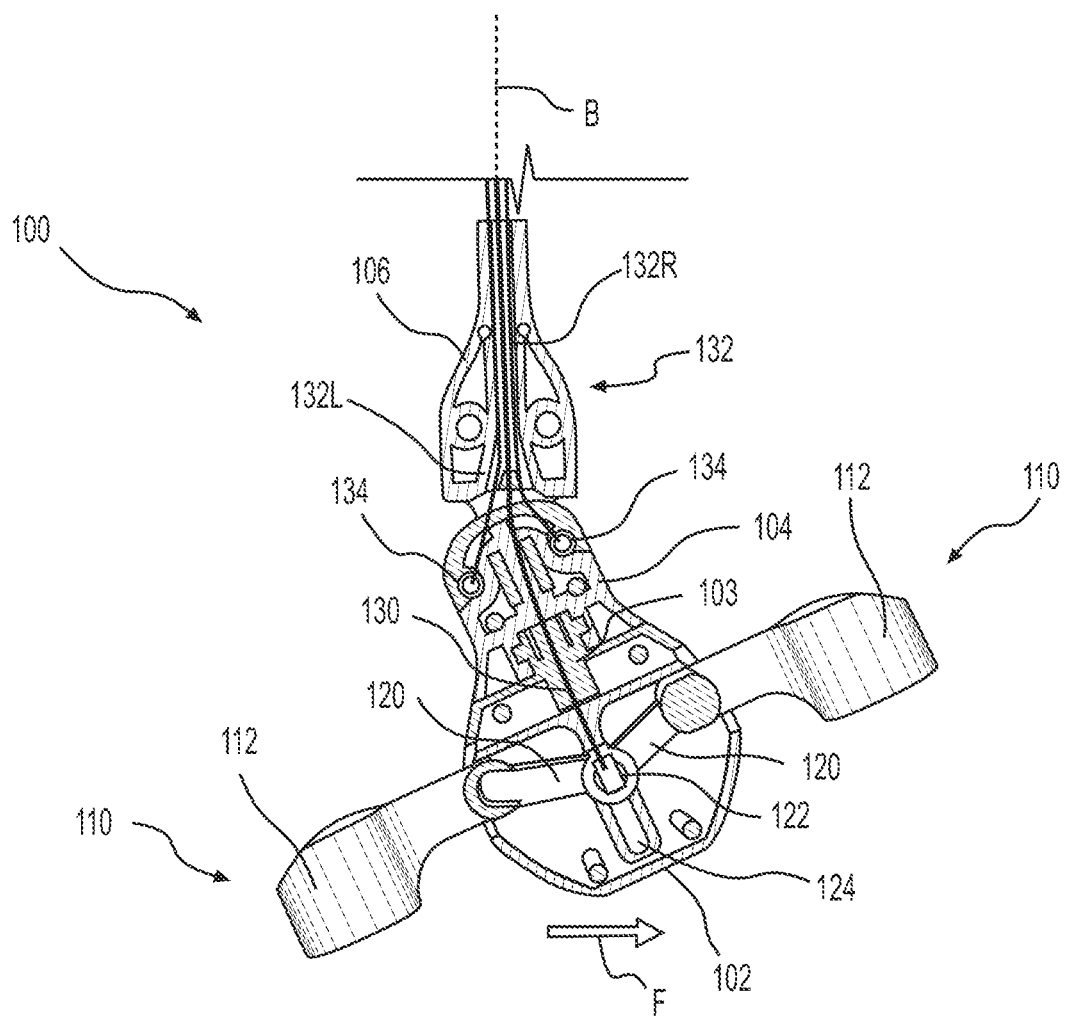
FIG. 5A is a cross-sectional top view of the medical device of FIG. 1 in a first pivot position, according to aspects of this disclosure.
Figure 5B:
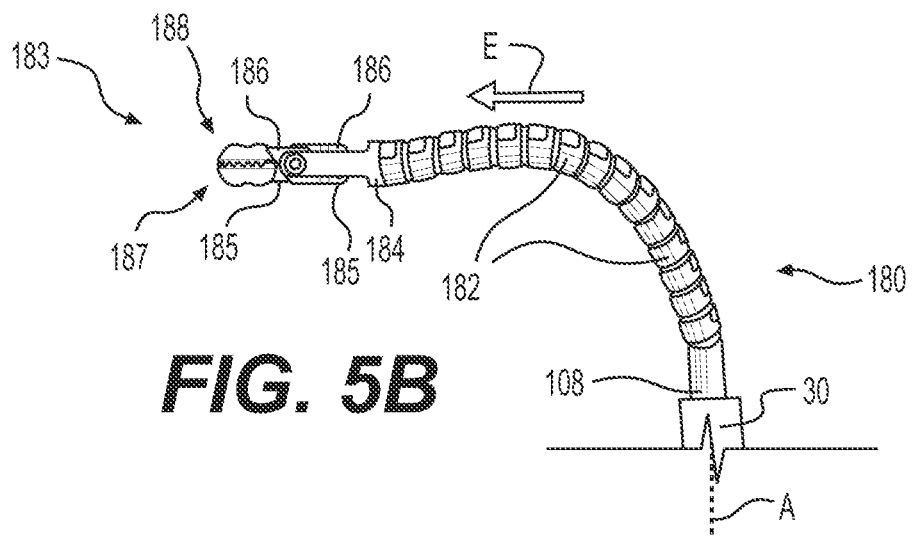
FIG. 5B is a partial top view of the grasper assembly of the medical device of FIG. 1 in a first articulated position, according to aspects of this disclosure.

Referring to FIGS. 5A-5B, the medical device 100 may be further actuated by moving the handle assembly 102 and the movable body 104 relative to the fixed body 106 to articulate the articulation joint 180. For example, the handle assembly 102 and the movable body 104 may be pivoted in a direction F relative to the central axis B of the fixed body 106 (e.g., rightward). In this instance, with the pair of drive wires 132 disposed within the movable body 104 and secured thereto at the connection points 134, the drive wires 132 are actuated when the handle assembly 102 and the movable body 104 moves, thereby articulating the articulation joint 180. Movement of the handle assembly 102 and the movable body 104 in the direction F may provide a proximal retraction (e.g., pulling) of at least one of the drive wires 132, and a simultaneous distal extension of the other drive wire 132. For example, movement of the handle assembly 102 and the movable body 106 in the direction F may provide a tensioning of at least one of the drive wires 132 and a simultaneous relaxing (e.g., omission of force) of the other drive wire 132.

As described above, with each of the pair of drive wires 132 secured to opposing sides/portions of the distal-most articulation link 182 of the plurality of articulation links 182 (e.g., adjacent to the clevis 184), the articulation joint 180 is operable to articulate (e.g., bend, pivot, deflect, etc.) in a direction of the drive wire 132 that is retracted/tensioned (e.g., pulled) proximally. In this instance, the drive wire 132 positioned relative to the handle assembly 102 along a side opposite of the direction F (e.g., a left drive wire 132L) is tensioned and thereby pulled proximally relative to the opposing drive wire 132 (e.g., a right drive wire 132R). Accordingly, the drive wire 132 positioned relative to the handle assembly 102 along a side adjacent to the direction F (e.g., the right drive wire 132R) is relaxed and/or extended distally relative to the opposing drive wire 132 described above (e.g., the left drive wire 132L). As such, the plurality of articulation links 182 of the articulation joint 180 may be articulated in a direction E relative to the longitudinal axis A of the fixed body 106 (e.g., leftward) and the end effector 183 is moved accordingly.

Figure 6A:
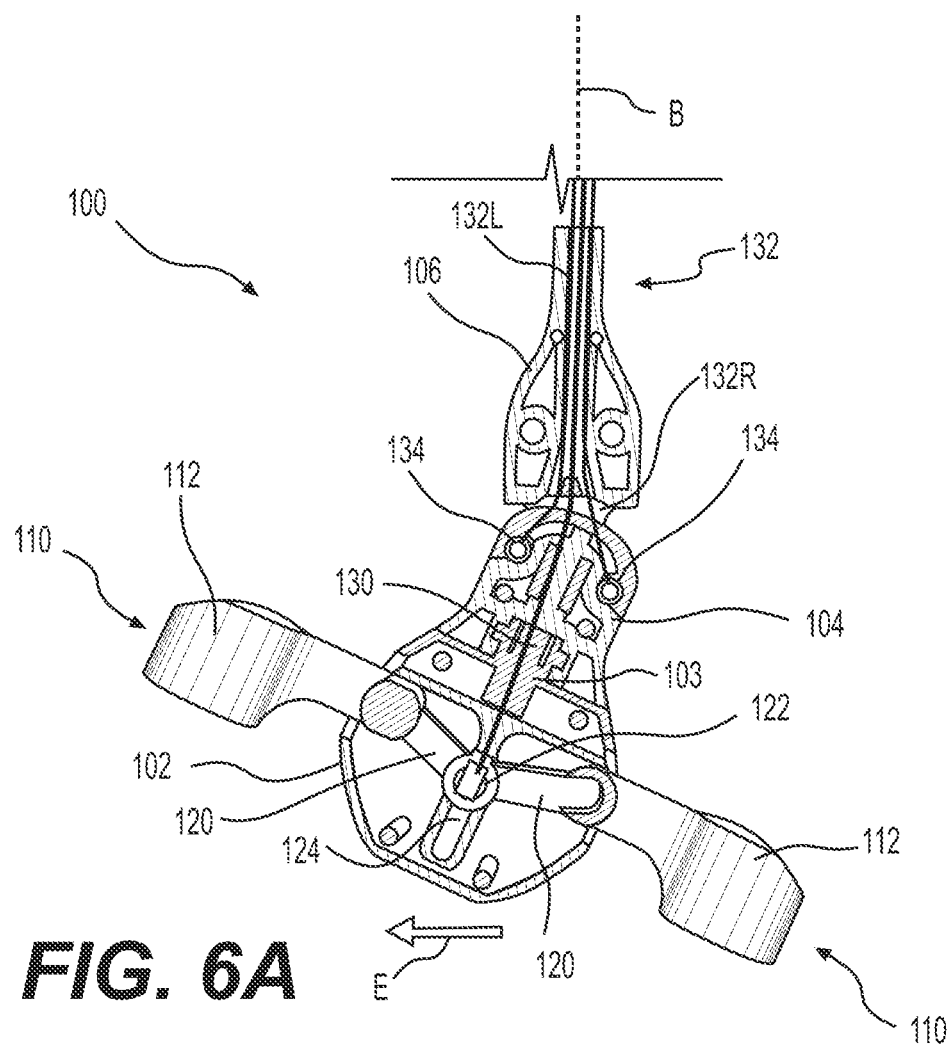
FIG. 6A is a cross-sectional top view of the medical device of FIG. 1 in a second pivot position, according to aspects of this disclosure.
Figure 6B:
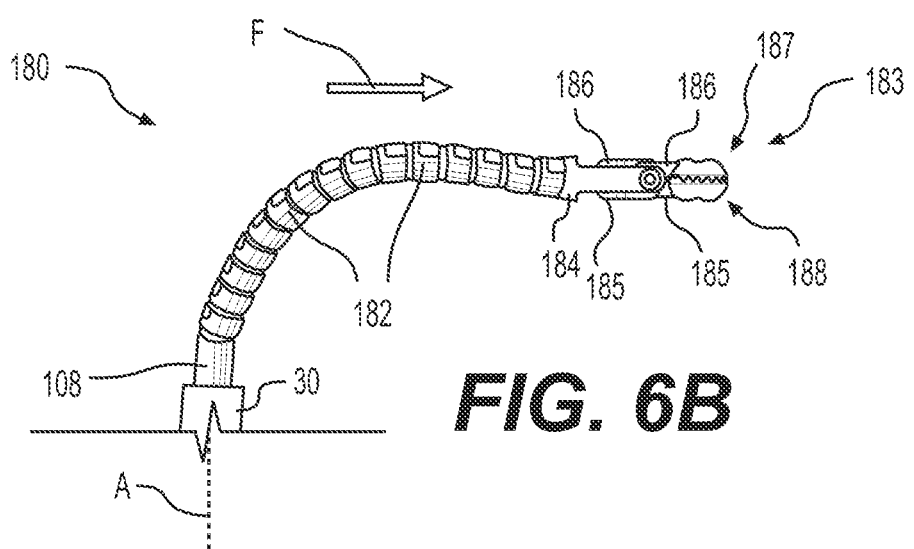
FIG. 6B is a partial top view of the grasper assembly of the medical device of FIG. 1 in a second articulated position, according to aspects of this disclosure.

Additionally and/or alternatively, now referring to FIGS. 6A-6B, the medical device 100 may be actuated by moving (e.g., pivoting) the handle assembly 102 and the movable body 104 in a direction E, opposite direction F, relative to the central axis B of the fixed body 106 (e.g., leftward) to articulate the articulation joint 180. In this instance, the drive wires 132 are actuated in the direction E and at least one of the drive wires 132 are retracted (e.g., pulled) proximally while the other drive wire 132 is relaxed and/or extended distally. As described above, the articulation joint 180 is operable to articulate (e.g., bend, pivot, deflect, etc.) in a direction of the drive wire 132 that is tensioned and/or retracted (pulled) proximally.

In this instance, the drive wire 132 positioned relative to the handle assembly 102 along a side opposite of the direction E (e.g., the right drive wire 132R) is tensioned and thereby pulled proximally relative to the opposing drive wire 132 (e.g., the left drive wire 132L). The drive wire 132 positioned relative to the handle assembly 102 along a side adjacent to the direction E (e.g., the left drive wire 132L) is relaxed and/or extended distally relative to the opposing drive wire 132 described above (e.g., the right drive wire 132R). Accordingly, the plurality of articulation links 182 of the articulation joint 180 is articulated in the direction F relative to the longitudinal axis A of the fixed body 106 (e.g., rightward), and the end effector 183 is moved accordingly.

Each of the aforementioned devices, assemblies, and methods may be used to facilitate access to a target treatment site and provide enhanced control of ancillary tools/devices (end effector) for use at the target treatment site. By providing a medical device with a handle assembly capable of controlling and moving a plurality of tools/devices coupled to the medical device, a user may interact with a target treatment site using the various tools/devices of the medical instrument during a procedure via an intuitive interface of the handle assembly. In this instance, a user may reduce overall procedure time, increase efficiency of procedures, and/or avoid unnecessary harm to a subject's body caused by limited control of the ancillary tools/devices.

It will be apparent to those skilled in the art that various modifications and variations may be made in the disclosed devices and methods without departing from the scope of the disclosure. Other aspects of the disclosure will be apparent to those skilled in the art from consideration of the specification and practice of the features disclosed herein. It is intended that the specification and examples be considered as exemplary only.

We claim:

1. A medical device, comprising:
a handle including a fixed body and a movable body, wherein the movable body is movable relative to the fixed body, and wherein the handle includes a proximal end, a distal end, and a longitudinal axis extending from the proximal end to the distal end;
a shaft extending from the fixed body;
an end effector at a distal end of the shaft; and
a lock, in a locked state of the movable body and the fixed body, configured to fix the movable body relative to the fixed body such that rotation of the movable body provides rotation of the fixed body,
wherein the lock, in an unlocked state of the movable body and the fixed body, permits rotation of the movable body relative to the fixed body, and thereby permits rotation of the end effector relative to the shaft, and wherein rotation of the movable body with rotation of the fixed body in the locked state permits rotation of the end effector with the shaft,
wherein deflection of the movable body relative to the fixed body permits deflection of the end effector relative to the fixed body,
wherein the handle includes a first actuator extending radially outward from the longitudinal axis to a first side of the handle, and a second actuator extending radially outward from the longitudinal axis to a second side of the handle opposite the first side,
wherein the first actuator and the second actuator translate radially inward relative to the longitudinal axis while transitioning the end effector from an unactuated state to an actuated state.

2. The medical device of claim 1, wherein each of the first and second actuators is sized to receive at least one finger or digit of a user.

3. The medical device of claim 1, wherein the first and second actuators include a coupler disposed within the handle and coupled to a slider that is received within an inner slot of the handle.

4. The medical device of claim 3, wherein, in the actuated state of the handle, the coupler is configured to move the slider to the proximal end of the handle.

5. The medical device of claim 1, further comprising a rotation joint disposed within and fixed to the handle, wherein the rotation joint is coupled to a first end of an actuation wire, wherein a second end of the actuation wire is coupled to the end effector.

6. The medical device of claim 5, wherein the rotation joint is configured to rotate the actuation wire and the end effector in response to rotation of the movable body relative to the fixed body.

7. The medical device of claim 1, further comprising a pair of drive wires coupled to and extending between the movable body and the distal end of the shaft.

8. The medical device of claim 7, wherein the movable body is configured to translate the pair of drive wires within the movable body to deflect the end effector relative to the fixed body when the movable body is deflected relative to the fixed body.

9. The medical device of claim 1, further comprising an actuation wire coupled to and extending between the movable body and the end effector.

10. The medical device of claim 9, wherein, in an actuated state of the handle, the actuation wire is tensioned so as to actuate the end effector.

11. The medical device of claim 10, wherein the end effector includes a pair of jaws, and wherein in the actuated state, the pair of jaws are closed and/or approximate one another.

12. The medical device of claim 1, further comprising a connector assembly including a first clasp and a second clasp, wherein the first clasp is operable to attach the connector assembly to the handle and the second clasp is operable to attach the connector assembly to an instrument, thereby fixing the handle relative to the instrument.

13. A medical device comprising:
a shaft assembly;
an end effector at a distal end of the shaft assembly;
a handle at a proximal end of the shaft assembly,
    wherein handle includes a proximal portion and a distal portion, and wherein the handle includes a proximal end, a distal end, and a longitudinal axis extending from the proximal end of the handle to the distal end of the handle; and
a lock configured to rotatably fix the proximal portion relative to the distal portion when the lock is engaged,
    wherein the handle is configured such that:
        when the lock is not engaged, rotation of the proximal portion relative to the distal portion rotates the end effector relative to the shaft assembly,
        simultaneous rotation of the proximal portion and the distal portion rotates the end effector and the shaft assembly together when the lock is engaged, and
        deflection of the proximal portion relative to the distal portion deflects the end effector relative to the shaft assembly;
    wherein the handle includes an actuator extending from inside the proximal portion, through an opening of a sidewall of the proximal portion, and radially outward from the proximal portion relative to the longitudinal axis of the handle,
    wherein the actuator translates through the opening of the sidewall while transitioning the end effector from an unactuated state to an actuated state.

14. The medical device of claim 13, wherein the handle being configured such that:
translation of the actuator inward relative to the proximal portion actuates the end effector to a first configuration; and
translation of the actuator outward relative to the proximal portion actuates the end effector to a second configuration.

15. The medical device of claim 13, further comprising an actuation wire including a first end coupled to the proximal portion and a second end coupled to the end effector; and
    wherein the actuation wire is configured to rotate the end effector in response to rotation of the proximal portion relative to the distal portion.

16. The medical device of claim 13, further comprising a pair of drive wires, each of the drive wires including a first end coupled to the proximal portion and a second end coupled to the end effector; and
    wherein the pair of drive wires are configured to deflect the end effector relative to the shaft assembly in response to deflection of the proximal portion relative to the distal portion.

17. A medical device comprising:
a first body;
a second body extending distally from the first body,
    wherein the first body is laterally pivotable and rotatable relative to the second body;
an end effector extending distally from the second body;
a lock, in a locked state of the first body and the second body, configured to fix the first body relative to the second body such that rotation of the first body provides rotation of the second body,
wherein the first body is configured to:
    rotate the end effector relative to the second body when the lock is in an unlocked state, via rotation of the first body independent of the second body;
    rotate the end effector with the second body when the lock is in the locked state, via rotation of the first body concurrently with the second body; and
    pivot the end effector relative to the second body when the first body pivots independent of the second body; and
a first actuator and a second actuator, the first actuator extending from inside the first body through a first opening of a first sidewall of the first body and radially outward from the first body relative to a longitudinal axis of the medical device, the second actuator extending from inside the first body through a second opening of a second sidewall of the first body and radially outward from the first body relative to the longitudinal axis of the medical device, the first actuator translates through the first opening and the second actuator translates through the second opening while transitioning the end effector from an unactuated state to an actuated state,
wherein, the first actuator and the second actuator extend radially outward from inside the first body to exterior the first body, the first actuator and the second actuator translate radially inward relative to the longitudinal axis of the medical device while transitioning the end effector from the unactuated state to the actuated state.

18. The medical device of claim 17, wherein the first actuator and the second actuator each includes a coupler disposed within the first body and coupled to a slider that is received within an inner slot of the first body.

19. The medical device of claim 18, wherein, in the actuated state of the end effector, the couplers are configured to move the slider to a proximal end of the first body.

20. The medical device of claim 1, wherein each of the first actuator and the second actuator extends from the movable body of the handle.

* * * * *